United States Patent [19]

Lindwurm et al.

[11] 4,419,524
[45] Dec. 6, 1983

[54] PROCESS FOR THE PREPARATION OF DIHALOVINYLCYCLOPROPANECARBOXYLIC ACIDS

[75] Inventors: Ferenc Lindwurm; József Muskovits; Sándor Zoltán; Rezsö Kolta; Rudolf Soós; Tivadar Puskás; Éva Somfai; György Hidasi, all of Budapest, Hungary

[73] Assignee: Chinoin Gyogyszer Es Vegyeszeti Termekek Gyara Rt, Budapest, Hungary

[21] Appl. No.: 350,424

[22] Filed: Feb. 19, 1982

[30] Foreign Application Priority Data

Feb. 20, 1981 [HU] Hungary ........................ 411

[51] Int. Cl.³ .................................. C07C 69/743
[52] U.S. Cl. ........................................ 562/506
[58] Field of Search .................... 560/124; 562/506

[56] References Cited

U.S. PATENT DOCUMENTS

| | | | |
|---|---|---|---|
| 3,943,167 | 3/1976 | Suzukamo | 562/506 |
| 4,024,163 | 5/1977 | Elliott | 562/506 |
| 4,288,610 | 9/1981 | Rumanowski | 560/124 |
| 4,306,077 | 12/1981 | Leigh | 562/506 |

FOREIGN PATENT DOCUMENTS 2713538  9/1978  Fed. Rep. of Germany ...... 562/506

OTHER PUBLICATIONS

Starks, "Phase Transfer Catalysis Principles and Techniques," pp. 1-9 (1978).

*Primary Examiner*—Michael L. Shippen
*Attorney, Agent, or Firm*—Karl F. Ross; Herbert Dubno

[57] ABSTRACT

The invention relates to a new process for the preparation of cyclopropanecarboxylic acids of the formula (I)

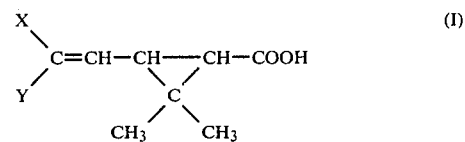

wherein
X and Y independently stand for halogen, by the alkaline hydrolysis of the corresponding alkyl esters having 1 to 6 carbon atoms in the alkyl moiety, in or without a water-miscible organic solvent, in the presence of a phase transfer catalyst. The hydrolysis is carried out with a 2 to 50% by weight aqueous alkali hydroxide solution. If desired, under suitable conditions the cis/trans ratio of the original ester can be altered in the end products. The cyclopropanecarboxylic acids of the formula (I) are obtained in a high purity and are useful intermediates of insecticidally active pyrethroids.

10 Claims, No Drawings

PROCESS FOR THE PREPARATION OF DIHALOVINYLCYCLOPROPANECARBOXYLIC ACIDS

FIELD OF THE INVENTION

The invention relates to a new process for the preparation of cyclopropanecarboxylic acids in high purity. In particular, the invention concerns a process for preparing dihalovinyl cyclopropanecarboxylic acids of the formula (I)

$$\begin{array}{c}X\\ \phantom{X}\diagdown\\ \phantom{XX}C=CH-CH-\!\!-\!\!-CH-COOH\\ \phantom{XX}\diagup\quad\diagdown\,\diagup\\ Y\quad\quad\quad\quad\quad C\\ \phantom{XXXXXX}\diagup\,\diagdown\\ \phantom{XXXXXX}CH_3\quad CH_3\end{array}\quad (I)$$

wherein

X and Y independently stand for halogen, by hydrolysis of the corresponding esters of the formula (II)

$$\begin{array}{c}X\\ \phantom{X}\diagdown\\ \phantom{XX}C=CH-CH-\!\!-\!\!-CH-COOR\\ \phantom{XX}\diagup\quad\diagdown\,\diagup\\ Y\quad\quad\quad\quad\quad C\\ \phantom{XXXXXX}\diagup\,\diagdown\\ \phantom{XXXXXX}CH_3\quad CH_3\end{array}\quad (II)$$

wherein

R is alkyl having 1 to 6 carbon atoms.

X and Y preferably stand for chlorine or bromine.

According to another aspect of the invention there is provided a method for the preparation of an ester and carboxylic acid containing the cis-isomers and trans-isomers in a desired ratio from a mixture of cis-esters and trans-esters of the formula (II), in which R, X and Y are as defined above.

The invention further relates to a process for preparing a pure carboxylic acid from a contaminated ester of the formula (II), in which R, X and Y are as defined above, by reacting said ester with a 2 to 50% by weight aqueous solution of an alkali metal hydroxide, in the presence of a water-immiscible organic solvent or in the absence of any solvent, in the presence of a phase transfer catalyst.

(a) According to a variant of the latter reaction the alkali hydroxide solution is employed in 100 to 150% by weight of its equivalent amount to preserve the original isomeric ratio.

(b) If the isomeric ratio is to be adjusted to a desired value, about 70 to 110% by weight of the alkali metal hydroxide equivalent with the trans isomer present in the starting ester is used.

Thereafter an aliphatic hydrocarbon having 5 to 10 carbon atoms is added to the reaction mixture containing the hydrolysis product, the pH of the mixture is adjusted to acidic and the free carboxylic acid obtained is isolated from the hydrocarbon phase by selective crystallization. If the starting carboxylic acid ester of the formula (II) contained impurities, the by-product of ester synthesis are eliminated from the reaction mixture obtained by hydrolysis, by steam distillation.

BACKGROUND OF THE INVENTION

Insecticidally active pyrethroids, e.g. cinerin, allethrin, phthaltrin, permetrin, cypermetrin, decametrin, are generally synthesized starting from a lower aliphatic ester of a corresponding cyclopropanecarboxylic acid. Pyrethroids can conveniently be prepared by hydrolyzing these esters into the corresponding free acids and coupling the acids obtained with the alcohol components of the desired active compounds by conventional techniques of esterification.

The conventionally employed hydrolysis methods have numerous disadvantages.

Alkaline hydrolysis of dihalovinylcyclopropanecarboxylic acid esters results in the formation of haloacetylenecyclopropanecarboxylic acid by-products, which are very difficult to eliminate. Therefore these methods are practically not suitable to prepare the desired active pyrethroid compound in a pure form. Attempts have been made to perform hydrolysis under acidic conditions but the purity of the products was not satisfactory and therefore they had to be recrystallized.

By the known methods mixtures of cis- and trans-cyclopropanecarboxylic acid esters are produced. (Coll. Czech. Commun. 242230 (1959)). The activity of pyrethroid compounds prepared from the two isomers is considerably different. It may therefore be desirable to separate the isomers. The methods known in the art generally relate to the separation of the cis- and trans-free acids, preferably by recrystallization from suitable solvents (J.Chem.Soc. 283, 1945).

OBJECT OF THE INVENTION

Our object was to provide a simple, large-scale process by which a pure product can be obtained by hydrolysis of cyclopropanecarboxylic acid esters, from a mixture of isomers the trans-isomer can be hydrolysed selectively and dihalovinylcyclopropanecarboxylic acids can be prepared without accompanying haloacetylene derivative impurities.

SPECIFIC DESCRIPTION

It has surprisingly been found that the esters of the formula (II) can be hydrolyzed also with aqueous alkali metal hydroxide solutions, if a suitable alkaline concentration is ensured and a small amount of a phase transfer catalyst is present to facilitate the heterogenous reaction with the aqueous alkali metal hydroxide solutions used for hydrolysis. It has further been found that the velocity of the hydrolysis of trans isomers exceeds that of the cis isomers, and accordingly, the two isomers can be separated with a good selectivity when suitable reaction conditions are employed. By this method the desired acid is obtained in a pure form, devoid of undesirable haloacetylene derivatives. The method is equally suitable for a total and a selective hydrolysis, for the preparation of pure acid from esters containing not-hydrolyzable impurities, for the separation of impurities and for the recovery of cyclopropanecarboxylic acids from synthesis by-products.

Hydrolysis is carried out with an aqueous solution of alkali metal hydroxides. Generally 2 to 50, preferably 4 to 30% by weight solutions of alkali metal hydroxides are used.

As the alkali metal hydroxide preferably sodium hydroxide and/or potassium hydroxide is employed.

The hydrolysis is accomplished at a temperature between 20° C. and the boiling temperature of the reaction mixture, preferably 50° C. and 100° C. Lower alkali concentration and lower temperature improve selectivity of the hydrolysis, and portionwise addition of the alkali metal hydroxide solution suppress the formation of by-products.

In case of a partial hydrolysis the alkali metal hydroxide solution is added in an amount corresponding to 70 to 110% preferably 80 to 95% of the amount equivalent with the trans ester isomer, in small portions.

The phase transfer catalyst should be alkali resistant. Its concentration in the reaction mixture is 0.01 to 5%, preferably 0.1 to 1%.

After the partial hydrolysis the unhydrolyzed ester enriched in the cis-isomer or the not hydrolyzable impurities may be separated from the aqueous phase on the basis of their different specific weight, may be dissolved by a suitable solvent, e.g. chlorinated solvents, aliphatic or aromatic hydrocarbons, or may be evaporated by steam distillation.

From the aqueous solutions containing salts of cyclopropanecarboxylic acid the acid can be set free by a mineral acid, preferably in situ in a petrol (gasoline) phase.

Cyclopropanecarboxylic acid obtained has a high purity and can be used for the preparation of pyrethroid insecticides without further purification.

Further details of the invention are illustrated by the following examples, which are not intended to limit the scope of the invention in any way.

EXAMPLE 1

27.9 g. of 2,2-dimethyl-3-(2,2-dichlorovinyl)cyclopropane-1-carboxylic acid ethyl ester (purity: 85%, cis) trans ratio: 40:60/, 6 g. of a 25% aqueous sodium hydroxide solution and 0.01 g. of sodium dodecylbenzene sulfonate are stirred at a temperature of 80° C. for 30 minutes. Hydrolysis is then continued with a further 5 g. portion of sodium hydroxide solution for 60 minutes and subsequently with an additional 5 g. portion of a sodium hydroxide solution for 150 minutes. The mixture is diluted with 30 ml. of water, cooled to 20° C. and the unreacted compounds are dissolved in 10 ml. of hexane. To the aqueous phase 80 ml. of hexane are added and the organic acid is set free by adding 12 g. of a 36% aqueous hydrochloric acid solution with stirring. The hexane solution is separated, decolored with 0.5 g. of activated carbon, filtered, 35 ml. of the solvent are distilled off and the residue is crystallized at −5° C. for 48 hours. The crystals are filtered off and dried. 17.8 g. (85%) of 2,2-dimethyl-3-(2,2-dichlorovinyl)-cyclopropane-1-carboxylic acid are obtained. Cis/trans ratio: 40:60.

EXAMPLE 2

36.2 g. of 2,2-dimethyl-3-(2,2-dibromovinyl)-cyclopropane-1-carboxylic acid ethylester (purity: 90%, cis) trans ratio: 45:65/, 4 g. of a 25% aqueous sodium hydroxide solution and 0.2 g. of tricaprylmethyl ammonium chloride are stirred at 100° C. for 30 minutes, whereupon three 4-g. portions of the sodium hydroxide solution are added in 30 minutes intervals and stirring is continued for altogether 240 minutes. The mixture is cooled to 20° C., diluted with 100 ml. of water and extracted with 10 ml. of benzene. The aqueous solution is admixed with 12 g. of a 36% aqueous hydrochloric acid solution at 70° C. and cooled to room temperature with stirring. The precipitated acid is dissolved in 60 ml. of benzene, the solution is separated and the solvent is evaporated. 30.0 g (92%) of 2,2-dimethyl-3-(2,2-dibromovinyl)-cyclopropanecarboxylic acid are obtained. Cis/trans ratio: 40:60.

EXAMPLE 3

24.7 g. of 2,2-dimethyl-3-(2,2-dichlorovinyl)-cyclopropane-1-carboxylic acid ethylester (purity: 96%, cis)-trans ratio: 40:60/, 0.1 g. of cetyltrimethylammonium bromide and 4 g. of a 20% aqueous sodium hydroxide solution are stirred at a temperature of 90° C. for 40 minutes, whereupon two 2-g. portions of a 40% aqueous sodium hydroxide solution are added in 40 minutes intervals and the hydrolysis is continued for altogether 200 minutes. 70 ml. of water are added, the mixture is cooled to 20° C. and the nonhydrolyzed phase is dissolved with 30 ml. of hexane. The hexane solution is decolored with activated carbon and filtered. The solvent is evaporated. 10.1 g. of a corresponding ester are obtained, in a purity of 90%. Cis/trans ratio: 85:15.

To the aqueous phase 60 ml. of hexane are added followed by the addition of 6.8 g. of a 36% aqueous hydrochloric acid solution. From the hexane solution of the free carboxylic acid hexane is removed. 12.2 g. of 2,2-dimethyl-3-(2,2-dichlorovinyl)-cyclopropane-carboxylic acid are obtained. Cis/trans ratio: 10:90.

EXAMPLE 4

24.7 g. of 2,2-dimethyl-3-(2,2-dichlorovinyl)-cyclopropane-1-carboxylic acid ethyl ester (purity: 96%, cis)trans ratio: 40:60), 6.7 g. of a 30% aqueous potassium hydroxide solution and 0.05 g. of polyoxyethylenesorbitane monooleate are stirred at 70° C. for 60 minutes. Stirring is continued with a further 6-g. portion of the potassium hydroxide solution for 60 minutes and with an additional 6-g. portion for 120 minutes. The solution is diluted with 100 ml. of water and 40 ml. fraction is distilled off to remove volatile, non-hydrolyzed substances. To the residual aqueous solution 80 cm$^3$ of hexane is added followed by the addition of 12 g. of a 36% aqueous hydrochloric acid solution at 60° C. with stirring. The reaction mixture is then further manufactured as described in Example 1. 19.8 g. (95%) of 2,2-dimethyl-3-(2,2-dichlorovinyl)cyclopropane-1-carboxylic acid are obtained. Cis/trans ratio: 40:60.

EXAMPLE 5

100 kg. of 2,2-dimethyl-3-(2,2-dichlorovinyl)-cyclopropane-1-carboxylic acid ethyl ester (prepared by the so called "Farkas process",/Coll.Czech.Commun.242230 (1959)), 100 lit. of methanol of technical grade and 90 kg of a 20% by weight aqueous sodium hydroxide solution are admixed with stirring and the mixture is boiled for 2 hours. 100 lit. of water are then added and 200 ml. of aqueous methanol are distilled off by a suitable condenser. The distillate contains also the by-products derived from the ester synthesis. The mixture is then cooled to 25° C. and 300 lit. of gasoline are pumped into it followed by a slow addition of 50 lit. of a concentrated hydrochloric acid solution. After stirring for half an hour the lower phase is separated carefully. The petrol solution remained in the equipment is washed with water, dried, decoloured and 200 lit. of petrol are distilled off, whereupon carboxylic acid is crystallized with stirring. The product is filtered off and dried (90 kg.). From the mother liquor a second crop (30 kg.) is obtained. The mother liquor of the second crop is stored till further use. Altogether 120 kg. of 2,2-dimethyl-3-(2,2-dichlorovinyl)-cyclopropane-1-carboxylic acid are obtained. Yield: 80 to 82% when the starting material contained 90% of pure ester.

If the starting material contains 99 to 100% of pure ester, the yield is 98%, while starting from a material containing 80% of pure ester a 72% yield is obtained. Cis(trans ratio: 40:60. Melting point: 62° C.) in a Boetius equipment). Purity: 99.7 to 100.3% by weight of acidimetry. The product is homogenous according to the t.l.c. measurements.

We claim:

1. A process for the preparation of a carboxylic acid of the formula (I) having a given ratio of cis to trans isomers thereof

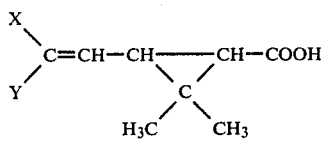

wherein

X and Y independently stand for halogen, which comprises the steps of:

(a) hydrolyzing a corresponding ester of the formula (II) having the same given ratio of cis to trans isomers thereof

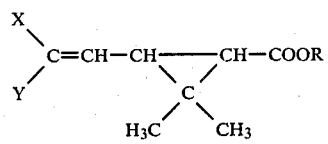

wherein

R is alkyl having 1 to 6 carbon atoms, with a 2 to 50% by weight aqueous solution of an alkali metalhydroxide, said alkali metal hydroxide present in an equivalent amount of 100% to 150% relative to the amount of the ester of the formula (II) present, in the presence of an alkali-resistant compound selected from the group consisting of sodium dodecyl benzenesulfonate, tricaprylmethyl ammonium chloride, cetyl trimethyl ammonium bromide, and polyoxyethylene sorbitane monooleate, the concentration of said compound amounting to 0.01 to 5% of the reaction mixture;

(b) adding an aliphatic hydrocarbon having 5 to 10 carbon atoms to the reaction mixture containing the hydrolysis product of step (a);

(c) adjusting the pH of the reaction mixture to an acidic pH by addition of an acid thereto; and (d) separating the free carboxylic acid of the formula (I) from the aliphatic hydrocarbon containing 5 to 10 carbon atoms.

2. The process defined in claim 1, step (a), wherein the hydrolysis is carried out in the presence of a water-miscible solvent selected from the group consisting of an alkanol and a water-soluble ether.

3. The process defined in claim 1, wherein X and Y are chlorine or bromine in the ester of the formula (II).

4. The process defined in claim 1, step (a), wherein the alkali metal hydroxide is present in an equivalent amount of 102 to 130% relative to the ester of the formula (II).

5. The process defined in claim 1, wherein following step (a), the reaction mixture is steam distilled to remove any contaminants which are by-products of ester synthesis.

6. A process for the preparation of a carboxylic acid of the formula (I) having a high trans to cis isomer ratio

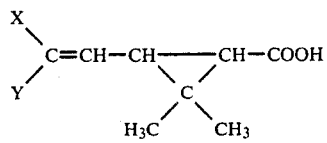

wherein

X and Y independently stand for halogen, which comprises the steps of:

(a) selectively hydrolyzing a corresponding ester of the formula (II) with a lower trans to cis isomer ratio

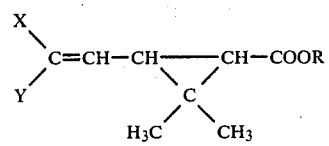

wherein

R is alkyl having 1 to 6 carbon atoms, with a 2 to 50% by weight aqueous solution of an alkali metal hydroxide, said alkali metal hydroxide present in an equivalent amount of 70 to 110% of the amount of the trans isomer of the ester of the formula (II) initially present, in the presence of an alkali-resistant compound selected from the group consisting of sodium dodecyl benzenesulfonate, tricaprylmethyl ammonium chloride, cetyl trimethyl ammonium bromide, and polyoxyethylene sorbitane monooleate, the concentration of said compound amounting to 0.01 to 5% of the reaction mixture, to form a nonhydrolyzed phase containing the ester of the formula (II) with a high cis to trans isomer ratio and a second hydrolyzed phase containing the acid of the formula (I) with a high trans to cis isomer ratio;

(b) adding an aliphatic hydrocarbon having 5 to 10 carbon atoms to the reaction of step (a) and removing the nonhydrolyzed phase from the hydrolyzed phase;

(c) adding an aliphatic hydrocarbon having 5 to 10 carbon atoms to the hydrolyzed phase;

(d) adjusting the pH of the hydrolyzed phase to an acid pH by addition of an acid thereto; and (e) separating the free acid of the formula (I) having a high trans to cis isomer ratio from the aliphatic hydrocarbon having 5 to 10 carbon atoms.

7. The process defined in claim 6, step (a), wherein the selective hydrolysis is carried out in the presence of a water-miscible solvent selected from the group consisting of an alkanol and a water-soluble ether.

8. The process defined in claim 6 wherein X and Y are each chlorine or bromine in the ester of the formula (II).

9. The process defined in claim 6, step (a), wherein the alkali metal hydroxide is present in an equivalent amount of 80 to 95% relative to the amount of the trans isomer of the ester of the formula (II) initially present.

10. The process defined in claim 6, wherein following step (a), the reaction mixture is steam distilled to remove any contaminants which are by-products of ester synthesis.

* * * * *